(12) United States Patent
Okamoto et al.

(10) Patent No.: US 6,476,247 B1
(45) Date of Patent: Nov. 5, 2002

(54) PROCESSES FOR THE PREPARATION OF ORGANOLUTHENIUM COMPOUNDS USEFUL FOR THIN FILM FORMATION BY CVD

(75) Inventors: Koji Okamoto, Hiratsuka (JP); Jun-ichi Taniuchi, Hiratsuka (JP); Masayuki Saito, Hiratsuka (JP)

(73) Assignee: Tanaka Kikinzoku Kogyo K.K., Tokyo (JP)

( * ) Notice: Subject to any disclaimer, the term of this patent is extended or adjusted under 35 U.S.C. 154(b) by 0 days.

(21) Appl. No.: 09/869,300

(22) PCT Filed: Dec. 5, 2000

(86) PCT No.: PCT/JP00/08596

§ 371 (c)(1),
(2), (4) Date: Jul. 19, 2001

(87) PCT Pub. No.: WO01/42261

PCT Pub. Date: Jun. 14, 2001

(30) Foreign Application Priority Data

Dec. 7, 1999 (JP) .............................................. 11-347010
Dec. 14, 1999 (JP) .............................................. 11-353966

(51) Int. Cl.[7] .......................... C07F 17/02; C23C 16/00
(52) U.S. Cl. ..................................... 556/136; 427/248.1
(58) Field of Search ........................ 556/136; 427/248.1

(56) References Cited

U.S. PATENT DOCUMENTS 5,130,172 A  7/1992  Hicks et al. ................. 427/252

FOREIGN PATENT DOCUMENTS

EP  769721 A1  4/1997
JP  2-292293 A  12/1990

OTHER PUBLICATIONS

Chem. Abstr., vol. 95, 1981, the abstract No. 204121, Issue, Shul'pin, G. B. "Reduction of Carbonyl to methylene groups in ferrocene and ruthenocene derivatives by sodium borhydrides in the presence of proton acids and Lewis acids", ZH. Obshch. Khim., 1981, vol. 51 No. 9, p. 2152–2153.

Primary Examiner—Porfirio Nazario-Gonzalez
(74) Attorney, Agent, or Firm—Arent Fox Kintner Plotkin & Kahn

(57) ABSTRACT

The disclosed is a method of producing two organic ruthenium compounds; i.e., bis(ethylcyclopentadienyl)ruthenium and (alkylcyclopentadienyl)cyclopentadienylruthenium, which are useful for producing thin film through CVD. In one aspect, the invention provides a method for producing bis(ethylcyclopentadienyl)ruthenium, including hydrogenating bis(acetylcyclopentadienyl)ruthenium in the presence of a catalyst. In another aspect, the invention provides a method of producing (alkylcyclopentadienyl)cyclopentadienylruthenium, including acylating bis(cyclopentadienyl)ruthenium with carboxylic anhydride in the presence of phosphoric acid as a catalyst, to thereby produce (acylcyclopentadienyl)cyclopentadienylruthenium, and reducing the (acylcyclopentadienyl)cyclopentadienyl ruthenium.

8 Claims, No Drawings

PROCESSES FOR THE PREPARATION OF ORGANOLUTHENIUM COMPOUNDS USEFUL FOR THIN FILM FORMATION BY CVD

CROSS-REFERENCE TO RELATED APPLICATIONS

This application is a national stage application filed under 35 U.S.C. 371 of International Application No. PCT/JP00/08596, filed Dec. 05, 2000.

1. Technical Field

The present invention relates to a method of producing an organic ruthenium compound for use in forming, through chemical vapor deposition, ruthenium thin film or ruthenium compound thin film.

2. Background Art

In recent years, thin film formed of a precious metal such as ruthenium, platinum, or iridium or thin film formed of an oxide thereof has been used as a material for forming an electrode in a capacitor included in ICs and LSIs. The reason for employment of these precious metals is that a thin film electrode produced from these precious metals is endowed with excellent electrode characteristics. Particularly, ruthenium and ruthenium compounds have become of interest in that these ruthenium species are expected to serve as mainstream materials for producing thin film electrodes.

Generally, ruthenium thin films and ruthenium compound thin films are produced through chemical vapor deposition (hereinafter referred to as CVD), because CVD facilitates production of thin film of uniform thickness and attains excellent step coverage (step covering performance). Therefore, CVD is expected to be a predominant process for producing a thin film electrode in the future, because CVD meets a demand of recent years for higher packaging density of circuits and electronic parts.

As source substances used in CVD, among metallic compounds, organometallic compounds are used in view of low melting point and ease of handling. Particularly, as an organic ruthenium compound, bis(cyclopentadienyl)ruthenium (ruthenocene) represented by Formula 1:

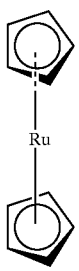

Formula 1 has conventionally been used.

Bis(cyclopentadienyl)ruthenium, having high stability in air and no toxicity, is a suitable source for CVD. However, this compound is in solid form at ambient temperature and has a melting point as high as approximately 199–201° C. Thus, a relatively large amount of energy is required for vaporizing the source.

In view of higher efficiency of thin film production, a variety of studies have been carried out on a ruthenium compound having a lower vaporization energy and lower melting point.

In order to lower the melting point of an organic ruthenium compound, there has been employed a method in which a functional group is added to at least one cyclopentadiene ring of bis(cyclopentadienyl)ruthenium, to thereby form a bis(cyclopentadienyl)ruthenium derivative.

Among such organic ruthenium compounds in which a functional group is added to a cyclopentadiene ring of bis(cyclopentadienyl)ruthenium, one promising candidate for a CVD source at present is bis(ethylcyclopentadienyl)ruthenium (also called 1,1'-diethylruthenocene), represented by Formula 2:

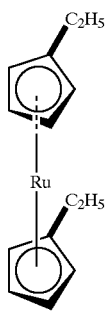

Formula 2 in which the functional group is added to each cyclopentadiene ring.

Bis(ethylcyclopentadienyl)ruthenium is in liquid form at ambient temperature and has a relatively low melting point, to thereby provide sufficient vapor pressure. Thus, this compound is regarded a suitable CVD source substance endowed with essential characteristics.

In addition, an organometallic compound, represented by Formula 3:

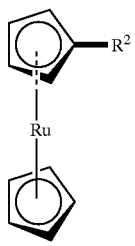

Formula 3

(wherein $R^2$ represents a linear or branched alkyl group) in which a functional group is introduced into only one cyclopentadiene ring of bis(cyclopentadienyl)ruthenium also shows promise as a CVD source.

For example, (ethylcyclopentadienyl)cyclopentadienylruthenium—$R^2$ is an ethyl group—has a melting point of approximately 12° C., which is remarkably lower than that of bis(cyclopentadienyl)ruthenium. Thus, this ethyl-substituted compound is considered to serve as an excellent CVD source in a source vaporization step and a step of transferring the formed gas source.

As methods of producing these bis(cyclopentadienyl)ruthenium derivatives, the following methods are known.

(1) Conventional Methods of Producing Bis(cyclopentadienyl)ruthenium

The following three methods for introducing an ethyl group into each cyclopentadiene ring of bis(cyclopentadienyl)ruthenium; i.e., methods for producing bis(ethylcyclopentadienyl)ruthenium, are known.

The first method is drawn to a method of producing bis(ethylcyclopentadienyl)ruthenium by reducing bis(acetylcyclopentadienyl)ruthenium by sodium borhydride ($NaBH_4$) (for detailed description of this production method, see G. B. Shul'pin, *Zh. Obshch. Khim.*, vol. 51, 2152 (1981)).

The second method is drawn to a method of producing bis(ethylcyclopentadienyl)ruthenium through ligand-exchange reaction between bis(ethylcyclopentadienyl)iron (($C_2H_5C_5H_4)_2Fe$) and ruthenium trichloride ($RuCl_3$) (for detailed description of this production method, see G. J. Gauthier, *Chem. Commun.*, 690 (1969)).

The third method is drawn to a method of producing bis(ethylcyclopentadienyl) ruthenium by reacting ethylcyclopentadiene ($C_2H_5C_5H_4$) and ruthenium trichloride ($RuCl_3$) in an alcoholic solvent in the presence of zinc powder (for detailed description of this production method, see Japanese Patent Application Laid-Open (Kokai) No. 11-35589).

(2) Conventional Methods of Producing Alkylcyclopentadienyl(cyclopentadifenyl)ruthenium Taking a method of producing (ethylcyclopentadienyl)cyclopentadienylruthenium as an example, a method of producing alkylcyclopentadienyl(cyclopentadienyl) ruthenium in which a functional group has been introduced into only one cyclopentadiene ring of bis(cyclopentadienyl) ruthenium is described next. In one known method, bis(cyclopentadienyl)ruthenium and acetic anhydride are reacted in the presence of aluminum chloride serving as a catalyst, to thereby form (acetylcyclopentadienyl) cyclopentadienylruthenium represented by the following Formula:

Formula 4

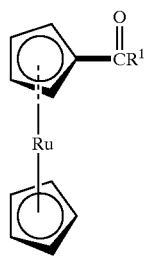

(wherein $R^1$ represents a linear or branched alkyl group) in which one hydrogen atom of bis(cyclopentadienyl) ruthenium is substituted by an acetyl group, and the thus-formed (acetylcyclopentadienyl)cyclopentadienylruthenium is reduced by aluminum chloride and lithium aluminum hydride ($LiAlH_4$), to thereby form (ethylcyclopentadienyl) cyclopentadienylruthenium (for detailed description of this technique, see M. D. Rausch et al., *J. Am. Chem. Soc.*, vol. 82, p76 (1960) and V. Mark et al., *Inorg. Chem.*, vol. 3, No. 7, p1067 (1964)).

However, when a functional group is introduced into a cyclopentadiene ring of bis(cyclopentadienyl)ruthenium through any of these conventional methods, to thereby produce a derivative thereof, the below-described problems arise. (3) Problems Involved in Conventional Methods of Producing Bis(ethylcyclopentadienyl)ruthenium.

Problems in connection with the aforementioned three conventional methods of producing bis(ethylcyclopentadienyl)ruthenium is described. In the first method, sodium—a component of sodium borohydride serving as a reducing agent—is intermingled as an impurity into produced bis(ethylcyclopentadienyl)ruthenium. As a result, sodium is also incorporated into the thin film prepared from this compound. Since an alkali metal such as sodium is an impurity which greatly affects electrical properties of the thin film, the bis(ethylcyclopentadienyl)ruthenium produced through the first method is not preferred as a CVD source substance.

The second method also involves a similar problem. Into bis(ethylcyclopentadienyl)ruthenium produced through the second method, an iron compound (ferrocene) having properties similar to those of bis(alkylcyclopentadienyl) ruthenium is intermingled. In addition, the iron compound is difficult to remove. Thus, when the bis(ethylcyclopentadienyl)ruthenium produced through the second method is used, a CVD apparatus and the thin film produced through CVD are also contaminated by the compound.

In terms of the purity of the product, the third method is more excellent that the other two methods. However, ethylcyclopentadiene which serves as a starting substance in this method is produced through pyrolysis of bis(ethylcyclopentadiene), which is generally difficult to obtain and is an expensive material. Thus, the produced bis(ethylcyclopentadienyl)ruthenium also becomes expensive, disadvantageously causing an increase in cost of semiconductor products. In addition, ethylcyclopentadiene has poor stability and is readily dimerized when allowed to stand at room temperature, to thereby form bis(ethylcyclopentadiene). Thus, difficulty in handling of ethylcyclopentadiene is problematic during production steps.
(4) Problems Involved in Conventional Methods of Producing Alkylcyclopentadienyl(cyclopentadienyl)ruthenium In a conventional method of producing alkylcyclopentadienyl(cyclopentadienyl)ruthenium, reactants are contaminated with aluminum originating from aluminum chloride serving as a catalyst and lithium aluminum hydride serving as a reducing agent, to thereby disadvantageously lower the purity of the produced (ethylcyclopentadienyl)cyclopentadienylruthenium. When (ethylcyclopentadienyl)cyclopentadienylruthenium of such a low purity is used to form thin film, aluminum serving as an impurity is intermingled into the formed thin film, thereby possibly deteriorating the electrical characteristics of the thin film. In addition, use of a low-purity source may cause contamination of a CVD apparatus.

Furthermore, aluminum chloride, which is used in both reaction steps, has poor stability and readily decomposes in air, to thereby produce hydrochloric acid gas. Accordingly, employment of the aforementioned known method may cause corrosion of an apparatus for producing (ethylcyclopentadienyl)cyclopentadienylruthenium, and a special means for anti-corroding is required, to thereby possibly elevate apparatus costs.

As mentioned above, conventional methods of producing bis(alkylcyclopentadienyl)ruthenium or alkylcyclopentadienyl(cyclopentadienyl)ruthenium raise problems in terms of product purity and production costs of target compounds.

The present invention has been accomplished in order to solve the aforementioned problems. Thus, an object of the present invention is to provide a method for producing bis(ethylcyclopentadienyl)ruthenium or alkylcyclopentadienyl(cyclopentadienyl)ruthenium—an organic ruthenium compound which can be employed as a CVD source—which method can produce such a compound at considerably high purity and low cost.

On the basis of the fact that conventionally known methods of producing (alkylcyclopentadienyl)

cyclopentadienylruthenium are limited only to production of (ethylcyclopentadienyl)cyclopentadienylruthenium, another object of the present invention is to provide a method of producing (alkylcyclopentadienyl)cyclopentadienylruthenium in which an alkyl group other than an ethyl group has been introduced, and to elucidate properties of the compound.

DISCLOSURE OF THE INVENTION

The present inventors have carried out extensive studies, and have found that a novel method of producing bis(ethylcyclopentadienyl)ruthenium or alkylcyclopentadienyl(cyclopentadienyl)ruthenium, which method differs from similar, conventional methods.

The methods of producing the respective organic ruthenium compounds is described next in detail.

(1) Method of Producing Bis(ethylcyclopentadienyl)ruthenium According to the Present Invention The method, which the present inventors hereby disclose, of producing bis(ethylcyclopentadienyl)ruthenium is drawn to a method, as recited in claim 1, of producing bis(ethylcyclopentadienyl)ruthenium represented by the below-described Formula 6:

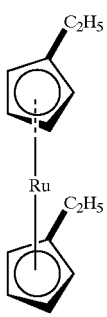

Formula 6 comprising hydrogenating bis(acetylcyclopentadienyl)ruthenium represented by the below-described Formula 5:

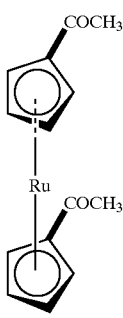

Formula 5 in the presence of a catalyst.

Claim 1 of the present invention provides a method of producing bis(ethylcyclopentadienyl)ruthenium, characterized by hydrogenating bis(acetylcyclopentadienyl)ruthenium, which is also employed as a starting material in the aforementioned first conventional method. According to the present invention, high-purity bis(ethylcyclopentadienyl)ruthenium can be produced, since the reaction system contains no latent impurity element; e.g., iron or an alkali metal such as sodium.

In the present invention, bis(acetylcyclopentadienyl)ruthenium serving as a starting material for producing bis(ethylcyclopentadienyl)ruthenium is a compound which can be produced readily at low cost. Thus, according to the present invention, bis(ethylcyclopentadienyl)ruthenium can be produced at low cost without use of expensive bis(ethylcyclopentadiene), which is employed in the aforementioned third conventional method.

The expression "in the presence of a catalyst" recited in claim 1 is based on the fact that hydrogenation of bis(acetylcyclopentadienyl)ruthenium of the present invention can be effected essentially in the presence of a catalyst. As recited in claim 2 of the present invention, catalysts such as a platinum catalyst, a palladium catalyst, a ruthenium catalyst, and the Raney nickel catalyst are preferably used. Examples of particularly preferred platinum catalysts include a platinum-carbon catalyst and a platinum oxide catalyst (the Adams catalyst).

The hydrogenation is carried out preferably under the following conditions: reaction temperature of room temperature to 150° C. and hydrogen pressure of $1\times10^5$ to $5\times10^6$ Pa.

As recited in claim 3, bis(acetylcyclopentadienyl)ruthenium is preferably obtained by reacting the bis(cyclopentadienyl)ruthenium represented by the below-described Formula 7:

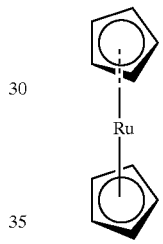

Formula 7 with acetic anhydride in the presence of a phosphoric acid catalyst.

As the catalyst, aluminum chloride ($AlCl_3$) could also be used. However, aluminum chloride is highly decomposable in air and generates hydrochloric acid gas, which is not preferable in operational circumstances and corrodes the reaction apparatus.

During production of bis(acetylcyclopentadienyl)ruthenium from bis(cyclopentadienyl)ruthenium, the ratio of the amount by mol of bis(cyclopentadienyl)ruthenium to that of acetic anhydride during reaction is preferably 1:2. When the amount of acetic anhydride is comparatively low, (acetylcyclopentadienyl)cyclopentadienylruthenium is intermingled into reaction products, thereby lowering the yield of bis(acetycyclopentadienyl)ruthenium from bis(cyclopentadienyl)ruthenium.

As recited in claim 4, the bis(cyclopentadienyl)ruthenium which is obtained by reacting cyclopentadiene and ruthenium chloride with zinc powder is preferably used. Cyclopentadiene is readily produced by pyrolizing dicyclopentadiene, which is contained in a large amount in crude benzene derived from tar and in cracked naphtha and is available in large amounts at low cost. Thus, according to the present invention, ruthenocene, furthermore bis(ethylcyclopentadienyl)ruthenium can be produced at low cost by use of cyclopentadiene as a starting material.

(2) Method of Producing Alkylcyclopentadienyl(cyclopentadienyl)ruthenium According to the Present Invention The method of producing alkylcyclopentadienyl(cyclopentadienyl)ruthenium according to the present invention is described next. The method, which the present inventors hereby disclose, of producing alkylcyclopentadienyl(cyclopentadienyl)ruthenium is, drawn the method according to claim 5, in which bis(cyclopentadienyl)ruthenium represented by Formula 8:

Formula 8

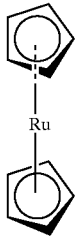

is acylated with carboxylic anhydride represented by the formula shown below:

$$(R^1CO)_2O \qquad \text{Formula 9}$$

(wherein $R^1$ represents a linear or branched alkyl group) in the presence of phosphoric acid serving as a catalyst, to thereby form (acylcyclopentadienyl)cyclopentadienylruthenium represented by the formula shown below:

Formula 10

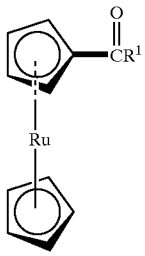

(wherein $R^1$ has the same meaning as mentioned above), and the thus-formed (acylcyclopentadienyl)cyclopentadienylruthenium is reduced, to thereby form (alkylcyclopentadienyl)cyclopentadienylruthenium represented by the formula shown below:

Formula 11

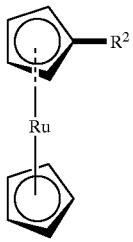

(wherein $R^2$ represents a linear or branched alkyl group).

Claim 5 of the present invention is based on the present inventors' finding that bis(cyclopentadienyl)ruthenium can readily be acylated by reaction with carboxylic anhydride in the presence of phosphoric acid serving as a catalyst. According to the present invention, high-purity (acylcyclopentadienyl)cyclopentadienylruthenium can be obtained, since aluminum chloride, which may generate an impurity, is not employed as a catalyst.

In claim 5 of the present invention, the (acylcyclopentadienyl) cyclopentadienylruthenium produced in the presence of a phosphoric acid catalyst is reduced, to thereby form (alkylcyclopentadienyl) cyclopentadienylruthenium. The term "reduction" in connection with claim 5 refers, in a broad sense, to a process for combining a compound with hydrogen to form a novel compound. However, in a manner similar to that employed in the aforementioned conventional method in which reduction is defined in a narrow sense, (alkylcyclopentadienyl) cyclopentadienylruthenium may be produced through reduction by use of aluminum chloride and lithium aluminum hydride. The criteria for employment of reduction by use of these reagents are that the (acylcyclopentadienyl) cyclopentadienylruthenium produced according to the present invention has high purity and that the purity of (alkylcyclopentadienyl)cyclopentadienylruthenium produced from the acyl compound is higher than that of (alkylcyclopentadienyl)cyclopentadienylruthenium produced through the conventional method.

However, in order to produce (alkylcyclopentadienyl) cyclopentadienylruthenium of higher purity, (acylcyclopentadienyl)cyclopentadienylruthenium is preferably reduced through hydrogenation as recited in claim 2. The reason for the employment of hydrogenation is that no reducing agent, such as aluminum chloride or lithium aluminum hydride, which possibly causes contamination is used, to thereby produce high-purity (alkylcyclopentadienyl)cyclopentadienylruthenium.

As described above, the present invention is characterized by enhancing the purity of products both in a step for converting bis(cyclopentadienyl)ruthenium to (acylcyclopentadienyl)cyclopentadienylruthenium and a step for converting (acylcyclopentadienyl)cyclopentadienylruthenium to (alkylcyclopentadienyl)cyclopentadienylruthenium.

The substituent $R^2$ of the produced (alkylcyclopentadienyl)cyclopentadienylruthenium can be formed into a desired substituent by selecting carboxylic anhydride to be reacted with bis(cyclopentadienyl)ruthenium. Some specific examples are shown in Table 1.

TABLE 1

| Carboxylic anhydrides | Formed (alkylcyclopentadienyl)-cyclopentadienylruthenium |
|---|---|
| Acetic | (Ethylcyclopentadienyl)-cyclopentadienylruthenium |
| Propionic | (n-Propylcyclopentadienyl)-cyclopentadienylruthenium |
| Isobutyric | (Isobutylcyclopentadienyl)-cyclopentadienylruthenium |
| Pivalic | (neo-Pentylcyclopentadienyl)-cyclopentadienylruthenium |
| n-Butyric | (n-Butylcyclopentadienyl)-cyclopentadienylruthenium |
| 2-Methylbutanoic | (2-Methylbutylcyclopentadienyl)-cyclopentadienylruthenium |
| n-Valeric | (n-Pentylcyclopentadienyl)-cyclopentadienylruthenium |
| Isopentanoic | (Isopentylcyclopentadienyl)-cyclopentadienylruthenium |

During the above reaction, the ratio of the amount by mol of bis(cyclopentadienyl)ruthenium to that of carboxylic anhydride is preferably 1:1; i.e., equivalent. When the amount of carboxylic anhydride is comparatively small, the yield of (acylcyclopentadienyl)cyclopentadienylruthenium decreases, whereas when the amount of carboxylic anhydride is comparatively large, bis(acylcyclopentadienyl) ruthenium—species in which two cyclopentadiene rings of bis(cyclopentadienyl)ruthenium are substituted—is simultaneously formed. In this case, the yield of (acylcyclopentadienyl)cyclopentadienylruthlenium also decreases.

In claim 5 of the present invention, (acylcyclopentadienyl)cyclopentadienylruthenium is formed through hydrogenation in a manner similar to that of claim 1. Accordingly, claim 5 also includes an expression "in the presence of a catalyst," to thereby clearly describe the requirement of the presence of a catalyst. As recited in claim 8, a catalyst such as a platinum catalyst, a palladium catalyst, a ruthenium catalyst, or the Raney nickel catalyst is preferably used. Examples of particularly preferred platinum catalysts include a platinum-carbon catalyst and a platinum oxide catalyst (the Adams catalyst).

In addition, hydrogenation is carried out preferably under the following conditions: reaction temperature of room temperature to 150° C. and hydrogen pressure of $1 \times 10^5$ to $5 \times 10^6$ Pa.

As described above, the species of (alkylcyclopentadienyl)cyclopentadienylruthenium produced through the method according to the present invention have high purity and contain no impurity such as aluminum. In addition, these compounds are in liquid form or solid form of low melting point at room temperature and have a high vapor pressure at approximately 100° C. Thus, these compounds are suitable for CVD sources.

BEST MODES FOR CARRYING OUT THE INVENTION

Regarding each organic ruthenium compound, suitable modes for carrying out the present invention is described next.

(1) Production of Bis(ethylcyclopentadienyl) ruthenium and Evaluation Thereof

Embodiment 1

Dicyclopentadiene (2000 g) was pyrolized at 180° C., to thereby form cyclopentadiene, and the thus-formed cyclopentadiene was purified through distillation at 40° C. To the purified cyclopentadiene (1500 g), ruthenium trichloride (130 g) and ethyl alcohol (2500 ml) were added, and the resultant reaction mixture was cooled to −10° C. After cooling was complete, zinc powder (163 g) was added to the reaction mixture in a divided (7 portions) manner at uniform intervals so as to allow the mixture to react. The resultant reaction mixture was subjected to extraction by use of benzene, and the product was recrystallized in hexane, to thereby yield 80 g of bis(cyclopentadienyl)ruthenium.

The thus-obtained bis(cyclopentadienyl)ruthenium (3 g), acetic anhydride (20 ml), and 85% phosphoric acid (2.0 ml) were placed in a round-bottom flask, and the mixture was heated at 85° C. for one hour. Subsequently, the reaction product was neutralized by use of sodium hydroxide. The neutralized mixture was subjected to extraction by use of hexane, thereby separating bis(acetylcyclopentadienyl) ruthenium.

The thus-produced bis(acetylcyclopentadienyl)ruthenium (10.8 g) was weighed and dissolved in methanol (300 cc), and a 5% Pd/C catalyst (1 g) was added to the resultant solution. The mixture was allowed to react at a hydrogen pressure of $3.45 \times 10^5$ Pa (50 psi) for 24 hours. The resultant reaction mixture was purified through distillation at 100° C. and $3.99 \times 10^{-3}$ Pa (0.3 torr), to thereby yield 5.7 g of bis(ethylcyclopentadienyl)ruthenium. The bis (ethylcyclopentadienyl)ruthenium was found to have a melting point of 6° C.

Embodiment 2

The procedure of Embodiment 1 was repeated, except that a 10% Pt/C catalyst was used instead of the 5% Pd/C catalyst, to thereby produce bis(ethylcyclopentadienyl) ruthenium.

Embodiment 3

The procedure of Embodiment 1 was repeated, except that a platinum oxide catalyst was used instead of the 5% Pd/C catalyst, to thereby produce bis(ethylcyclopentadienyl) ruthenium.

Embodiment 4

The procedure of Embodiment 1 was repeated, except that the Raney nickel catalyst was used instead of the 5% Pd/C catalyst, to thereby produce bis(ethylcyclopentadienyl) ruthenium.

COMPARATIVE EXAMPLE 1

To a solution of sodium borohydride dissolved in sulfuric acid, bis(acetylcyclopentadienyl)ruthenium (3.15 g) which had been produced in Embodiment 1 was added, and the mixture was allowed to react for 24 hours at room temperature. The organic phase of the resultant reaction mixture was separated by use of ethyl ether and purified through distillation, to thereby yield bis(ethylcyclopentadienyl) ruthenium.

COMPARATIVE EXAMPLE 2

Bis(ethylcyclopentadienyl)iron (1.48 g) and ruthenium chloride anhydrate (0.21 g) were placed in a flask and mixed. The resultant mixture was allowed to react for 24 hours in an oil bath at 250° C. After completion of reaction, the organic phase was separated through extraction and further purified, to thereby yield bis(ethylcyclopentadienyl) ruthenium.

COMPARATIVE EXAMPLE 3

Ethanol (200 ml) was placed in a flask in which the atmosphere had been substituted under vacuum by argon. Ruthenium chloride trihydrate (25.0 g) was added to the flask and dissolved in the ethanol, and the resultant solution was cooled to −30° C. To the solution, ethylcyclopentadiene (40 g) was added, followed by addition of zinc powder (purity 99.999%, 200 mesh) (9.55 g); to the resultant mixture in a divided (7 portions) manner at intervals of 10 minutes. After completion of reaction, the resultant liquid phase was collected and subjected, to extraction by use of hexane, to thereby yield bis(ethylcyclopentadienyl) ruthenium.

Measurement of Purity of the Respective Compounds 1:

Bis(ethylcyclopentadienyl)ruthenium samples obtained and purified in Embodiments 1 to 4 and Comparative Examples 1 to 3 were analyzed in terms of purity and species and concentrations of impurities. The analysis was carried out by means of a gas chromatograph and a gas chromatography-mass spectrometry analyzer. Specifically, when a peak attributed to a species other than bis (ethylcyclopentadienyl)ruthenium was observed, the peak was assigned to a compound through mass analysis, to thereby identify the structure and species thereof. Table 2 shows the thus-measured purity of bis (ethylcyclopentadienyl)ruthenium samples of the Embodiments of the present invention and the Comparative Examples and species and concentrations of impurities contained therein.

TABLE 2

| | Purity of bis(ethyl-cyclo-pentadienyl)-ruthenium | Impurities: species and concentration | |
|---|---|---|---|
| Embodiment 1 | 99.99% | — | |
| Embodiment 2 | 99.99% | — | |
| Embodiment 3 | 99.99% | — | |
| Embodiment 4 | 99.98% | — | |
| Comp. Ex. 1 | 98.57% | Ethylruthenocene | 0.71% |
| | | Bis(acetylcyclo-pentadienyl)ruthenium | 0.20% |
| | | 1-Ethyl-1'-acetyl-ruthenocene | 0.52% |
| Comp. Ex. 2 | 96.86% | 1,1'-Diethylferrocene | 2.51% |
| | | Ethylruthenocene | 0.40% |
| | | Ethylferrocene | 0.23% |
| Comp. Ex. 3 | 98.90% | Ethylruthenocene | 0.33% |
| | | Triethylruthenocene | 0.15% |
| | | Bis(ethylcyclo-pentadiene) | 0.62% |

As is clear from Table 2, the purity of bis(ethylcyclopentadienyl)ruthenium samples produced in Embodiments 1 to 4 is confirmed to be as considerably high as approximately 99.9%. In contrast, it is also confirmed that samples of the Comparative Examples contain a plurality of bis(cyclopentadienyl)ruthenium derivatives as impurities, and that the purity of these samples is low as compared with that of the samples of Embodiments 1 to 4. Although the impurity content is trivial, such an impurity level is still considered to affect the pyrolysis temperature and vapor pressure of bis(ethylcyclopentadienyl)ruthenium. In addition, use of bis(ethylcyclopentadienyl)ruthenium containing such a derivative as an impurity so as to form thin film greatly affects the step coverage (step covering performance) and causes contamination of a CVD apparatus.

Measurement of Purity of the Respective Compounds 2:

Impurity elements contained in bis(ethylcyclopentadienyl)ruthenium samples obtained and purified in Embodiments 1 to 4 and Comparative Examples 1 to 3 were measured through ICP-MS. The results are shown in Table 3.

TABLE 3

| | Element concentration (ppm) | | | | |
|---|---|---|---|---|---|
| | Na | K | B | Zn | Fe |
| Embodiment 1 | <0.5 | <0.5 | <1.0 | <1.0 | <1.0 |
| Embodiment 2 | <0.5 | <0.5 | <1.0 | <1.0 | <1.0 |
| Embodiment 3 | <0.5 | <0.5 | <1.0 | <1.0 | <1.0 |
| Embodiment 4 | <0.5 | <0.5 | <1.0 | <1.0 | <1.0 |
| Comp. Ex. 1 | 3.0 | 1.5 | 2.3 | <1.0 | <1.0 |
| Comp. Ex. 2 | <0.5 | <0.5 | <1.0 | <1.0 | 5.0 |
| Comp. Ex. 3 | <0.5 | <0.5 | <1.0 | 1.5 | <1.0 |

As shown in Table 3, the samples of Embodiments 1 to 4 contained impurity elements at levels below the detection limit, whereas impurities intermingled during production steps were detected in the samples of the Comparative Examples. Specifically, alkali metals—sodium and potassium—and boron originating from sodium borohydride serving as a reducing agent were detected in the sample of Comparative Example 1. In the sample of Comparative Example 2, iron originating from bis(cyclopentadienyl)iron serving as a reactant was detected. Further, in the sample of Comparative Example 3, zinc originating from zinc powder which had been added during a production step was detected. Although each impurity element was contained at a level of some ppm, the impurity of such a level may contaminate the produced thin film and a CVD apparatus. Thus, the ruthenium complex containing such impurities is not preferred as a source for use in production of electronic material thin films.

(2) Production of Alkylcyclopentadienyl (cyclopentadienyl)ruthenium and Evaluation Thereof Embodiment 5

Bis(cyclopentadienyl)ruthenium (3 g), acetic anhydride (10 ml), and 85% phosphoric acid (2.0 ml) were placed in a round-bottom flask, and the mixture was heated at 85° C. for one hour. The formed reaction product was neutralized by use of sodium hydroxide, recrystallized, and subjected to extraction by use of hexane, thereby yielding 1.8 g of (acetylcyclopentadienyl)cyclopentadienylruthenium.

The thus-produced (acetylcyclopentadienyl)cyclopentadienylruthenium (10.8 g) was weighed and dissolved in methanol (300 cc), and a 5% Pt/C catalyst (1 g) was added to the resultant solution. The mixture was allowed to react at a hydrogen pressure: of $5\times10^6$ Pa and 80° C. for 24 hours. The resultant reaction mixture was purified through distillation at 100° C. and $5.32\times10^{-3}$ Pa (0.4 torr), to thereby yield 5.1 g of (ethylcyclopentadienyl)cyclopentadienylruthenium. The (ethylcyclopentadienyl)cyclopentadienylruthenium a found to have a melting point of 12° C.

Embodiment 6

Bis(cyclopentadienyl)ruthenium (3 g), pivalic anhydride (10 ml), and 85% phosphoric acid (2.0 ml) were placed in a round-bottom flask. In a manner similar to that of Embodiment 1, the mixture was heated at 85° C. for one hour. The formed reaction product was neutralized by use of sodium hydroxide, recrystallized, and subjected to extraction by use of hexane, thereby yielding 2.1 g of (trimethylacetylcyclopentadienyl)cyclopentadienylruthenium.

The thus-produced (trimethylacetylcyclopentadienyl)cyclopentadienylruthenium (10.8 g) was weighed and dissolved in methanol (300 cc), and a 5% Pt/C catalyst (1 g) was added to the resultant solution. The mixture was allowed to react under reaction conditions similar to those employed in Embodiment 1. The resultant reaction mixture was similarly purified, to thereby yield 4.9 g of (neopentylcyclopentadienyl)cyclopentadienylruthenium.

COMPARATIVE EXAMPLE 4

Bis(cyclopentadienyl)ruthenium (1.2 g), aluminum chloride (1.5 g) serving as a catalyst, and dichloromethane (100 ml) were placed in a flask and mixed. While acetic anhydride (0.4 ml) was added dropwise to the flask, the mixture was allowed to react at 65° C. under stirring. To the reaction mixture, water was added so as to cause hydrolysis. After removal of dichloromethane, through distillation, the residue was purified through chromatography by use of alumina. The resultant benzene eluent was concentrated, to thereby yield 0.5 g of (acetylcyclopentadienyl) cyclopentadienylruthenium.

The thus-produced (acetylcyclopentadienyl)cyclopentadienylruthenium (2.7 g) was weighed, and aluminum chloride (1.33 g), lithium aluminum hydride (0.38 g), and ethyl ether (20 ml) were added thereto. The mixture was allowed to react at room temperature for 24 hours. After completion of reaction, the reaction product was decomposed by adding hydrous ether thereto, and the resultant mixture was filtered. The ether layer was collected and concentrated, to thereby yield 1.5 g. of (ethylcyclopentadienyl)cyclopentadienylruthenium.

Measurement of Purity of the Respective Compounds:

Impurity elements contained in the (ethylcyclopentadienyl) cyclopentadienylruthenium sample obtained and purified in Embodiment 5, in the (neopentylcyclopentadienyl)cyclopentadienylruthenium sample obtained and purified in Embodiment 6, and in the (ethylcyclopentadienyl)cyclopentadienylruthenium sample obtained and purified in the Comparative Example 4 were measured through ICP-MS and atomic absorption analysis. The results are shown in Table 4.

TABLE 4

|  | Impurity element concentration (ppm) | | |
| --- | --- | --- | --- |
|  | Al | Na | K |
| Embodiment 5 | <1.0 | <0.5 | <0.5 |
| Embodiment 6 | <1.0 | <0.5 | <0.5 |
| Comp. Ex. 4 | 4.0 | 1.0 | <0.5 |

As shown in Table 4, the samples of Embodiments 5 to 6 contained impurity elements at levels below the detection limit, whereas impurities intermingled during production steps were detected in the sample of Comparative Example 4. Specifically, aluminum originating from aluminum chloride serving as a catalyst and lithium aluminum hydride serving as a reducing agent were detected in the sample of the Comparative Example. Although each impurity element was contained at a level of some ppm, the impurity of such a level may contaminate the produced thin film and a CVD apparatus. Thus, the ruthenium complex containing such impurities is not preferred as a source for use in production of electronic material thin films.

Industrial Applicability

As described hereinabove, the present invention relates to a method of producing an organic ruthenium compound serving as a source for use in production of ruthenium thin film or ruthenium compound thin film through CVD; i.e., a method of producing bis(ethylcyclopentadienyl)ruthenium or (alkylcyclopentadienyl)cyclopentadienyl ruthenium.

According to the present invention, low-cost production of high-purity bis(ethylcyclopentadienyl)ruthenium and (alkylcyclopentadienyl)cyclopentadienylruthenium can be attained. These organic ruthenium compounds produced in accordance with the present invention contain no impurity such as a bis(ethylcyclopentadienyl)ruthenium derivative or an elemental alkali metal such as sodium.

Accordingly, the organic ruthenium compounds produced in accordance with the present invention attain good step coverage (step covering performance) during use thereof in a CVD process and production of thin films of excellent characteristics. Thus, the compounds are suitable sources for producing thin films.

What is claimed is:

1. A method for producing bis(ethylcyclopentadienyl)ruthenium represented by structural formula 2,

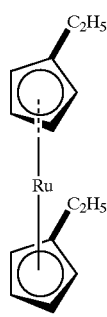

formula 2 comprising hydrogenating bis(acetylcyclopentadienyl)ruthenium represented by structural formula 1:

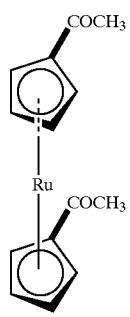

formula 1 in the presence of a catalyst.

2. A method for producing bis(ethylcyclopentadienyl)ruthenium according to claim 1, wherein any of a platinum catalyst, a palladium catalyst, a ruthenium catalyst, and the Raney nickel catalyst is employed as the catalyst.

3. A method for producing bis(ethylcyclopentadienyl)ruthenium according to claim 1, wherein bis(acetylcyclopentadienyl)ruthenium formed by reacting bis(cyclopentadienyl)ruthenium represented by Formula 3:

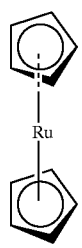

Formula 3 and acetic anhydride in the presence of a phosphoric acid catalyst is employed as the bis(acetylcyclopentadienyl)ruthenium.

4. A method for producing bis(ethylcyclopentadienyl)ruthenium according to claim 1, wherein bis(cyclopentadienyl)ruthenium formed by reacting cyclopentadiene, ruthenium chloride, and zinc powder is employed as the bis(cyclopentadienyl)ruthenium.

5. A method of producing (alkylcyclopentadienyl) cyclopentadienylruthenium represented by Formula 7,

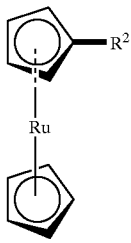

Formula 7

(wherein $R^2$ represents a linear or branched alkyl group) comprising acylating bis(cyclopentadienyl)ruthenium represented by Formula 4:

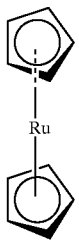

Formula 4 and carboxylic anhydride represented by Formula 5:

$(R^1CO)_2O$    Formula 5

(wherein $R^1$ represents a linear or branched alkyl group) in the presence of phosphoric acid as a catalyst, to thereby produce (acylcyclopentadienyl)cyclopentadienylruthenium represented by Formula 6:

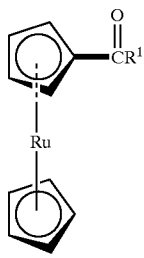

Formula 6

(wherein the substituent $R^1$ has the same meaning as mentioned above)

and reducing the (acylcyclopentadienyl) cyclopentadienylruthenium.

6. A method of producing (alkylcyclopentadienyl) cyclopentadienylruthenium according to claim 5, wherein the (acylcyclopentadienyl)cyclopentadienylruthenium is hydrogenated in the presence of a catalyst.

7. A method of producing (alkylcyclopentadienyl) cyclopentadienylruthenium according to claim 5, wherein the carboxylic anhydride to be reacted is acetic anhydride, propionic anhydride, isobutyric anhydride, pivalic anhydride, n-butyric anhydride, 2-methylbutanoic anhydride, n-valeric anhydride, or isopentanoic anhydride.

8. A method of producing (alkylcyclopentadienyl) cyclopentadienylruthenium according to claim 5, wherein a platinum catalyst, a palladium catalyst, a ruthenium catalyst, and the Raney nickel catalyst is employed as the catalyst.

* * * * *